United States Patent [19]
Takamori

[11] Patent Number: 5,474,068
[45] Date of Patent: Dec. 12, 1995

[54] MAGNETIC RESONANCE IMAGING APPARATUS

[75] Inventor: Hiromitu Takamori, Otawara, Japan

[73] Assignee: Kabushiki Kaisha Toshiba, Kawasaki, Japan

[21] Appl. No.: 321,575

[22] Filed: Oct. 11, 1994

Related U.S. Application Data

[63] Continuation of Ser. No. 257,951, Jun. 10, 1994, abandoned, which is a continuation of Ser. No. 65,136, May 20, 1993, abandoned.

[30] Foreign Application Priority Data

May 20, 1992 [JP] Japan ................................ 4-127538

[51] Int. Cl.$^6$ ................................................ A61B 5/055
[52] U.S. Cl. ........................... 128/653.2; 128/653.5; 242/378.2; 242/378.4; 324/318
[58] Field of Search ........................... 128/653.2, 653.5; 324/318, 322; 242/378.1, 378.2, 378.4

[56] References Cited

U.S. PATENT DOCUMENTS

| | | | |
|---|---|---|---|
| 3,106,368 | 10/1963 | Tait et al. | 242/107.1 |
| 4,972,852 | 11/1990 | Koob et al. | 128/653.2 |
| 5,065,760 | 11/1991 | Krause et al. | 128/653.5 |

FOREIGN PATENT DOCUMENTS

| | | |
|---|---|---|
| 62-119907 | 7/1987 | Japan . |
| 62-172227 | 10/1987 | Japan . |
| 62-268543 | 11/1987 | Japan . |

Primary Examiner—Ruth S. Smith
Attorney, Agent, or Firm—Ronald L. Yin; Limbach & Limbach

[57] ABSTRACT

The MR imaging apparatus is provided with a cable handling unit for handling an RF cable, which comprises a slack-preventing mechanism for winding the RF cable and feeding the RF cable according to a motion of a cradle, a cable guide mechanism for guiding the RF cable and a twist-preventing mechanism for preventing a twist of the RF cable. The slack-preventing mechanism comprises a reel for winding the RF cable and feeding the RF cable and a tension-imparting mechanism for imparting a tension to the RF cable. The cable guide mechanism comprises a stationary guide provided in the gantry and a moving guide having one end linked to the stationary guide slidably and another end linked to the cradle rotatably. The twist-preventing mechanism comprises a reel which can rotate according to a motion of the cradle, wherein the reel winds the RF cable loosely in a predetermined number of turns so that when the reel rotates in a predetermined direction, the number of turns decreases and when the reel rotates reversely, the number of turns increases.

5 Claims, 6 Drawing Sheets

MAGNETIC RESONANCE IMAGING APPARATUS

This is a continuation of application Ser. No. 08/257,951 filed on Jun. 10, 1994, now abandoned, which is a continuation of U.S. Ser. No. 08/065,136, filed on May 20, 1993, now abandoned.

BACKGROUND OF THE INVENTION

This invention relates to a magnetic resonance imaging (MRI) apparatus comprising of a cable handling unit for handling an RF cable for an RF coil.

SUMMARY OF THE INVENTION

An MRI apparatus holds a great advantage in medical use because of non-invasiveness or non X-ray dosing.

An MRI apparatus comprises an RF coil for transmitting an RF pulse to an object and receiving an MR signal from the object which can be reconstructed to image in a desired slice position of the object.

There are various types of the RF coils, for example, a whole body coil for covering a whole body of a patient and a surface coil, for example, a head coil or a neck coil, for covering only a predetermined portion of the patient.

When the head or neck coil is used, the coil is located near a head or a neck of the patient and a plug of the coil is plugged into a connector which is located in a top plate of a patient couch or a cradle.

Therefore, the coil can be close to the head or the neck and the head coil or the neck coil can detect an MR signal in a high S/N ratio.

The connector is electrically connected to a transmitting-receiving unit provided in a gantry using an RF cable.

The cradle can be lifted in a vertical direction so that the patient can easily lie on the cradle in a lower position and can be positioned in a predetermined level in an upper position. Furthermore, the cradle can be moved in a horizontal direction so that the patient can be moved into a cavity of the gantry(imaging area) and drawn out from the cavity and thus the connector is moved according to a motion of the cradle.

Therefore, the RF cable connected to the connector must be handled to prevent a slacking or an entanglement of the RF cable in a position between the connector and the transmitting-receiving unit.

The Japanese Patent Laid-Open Publication No. 62-268543, the Utility Model Laid-Open Publication No. 62-172227 and the Utility Model Laid-Open Publication No. 62-119907 disclose cable handling units for handling an RF cable provided in the MRI apparatus.

The cable handling unit disclosed in the Publication No. 62-268543 is provided under the cradle of the couch and comprises a plurality of reels for absorbing a slacking of an RF cable. The reels are mounted in a moving plate which can slide on a base plate and can move in a longitudinal direction according to a motion of the cradle.

The cable handling unit disclosed in the Publication No. 62-119907 is similarly provided under the cradle of the couch and can prevent the slacking of the RF cable.

However, many other mechanisms must be provided in the couch, for example, a lifting mechanism for lifting the cradle in a vertical direction and a moving mechanism for moving the cradle in a horizontal direction and when the cable handling unit is provided under the cradle, a structure in the couch becomes more complicated and the handling of the RF cable is very difficult.

Furthermore, the S/N ratio may decrease by an interaction between the RF cable and the RF coil because the RF cable is located near the RF coil.

The cable handling unit disclosed in the Publication No. 62-172227 is provided in the gantry and comprises an absorbing mechanism for absorbing a slacking of an RF cable. The absorbing mechanism turns down the RF cable in the gantry and can prevent the slacking of the RF cable.

However, the plug of the RF cable must be detached from the connector when the cradle is lowered and thus a medical examination time required for one patient or a "throughput" of the MRI apparatus decreases.

SUMMARY OF THE INVENTION

An object of this invention is to provide an MRI apparatus comprising a cable handling unit for handling an RF cable in a simple mechanism which can improve the throughput and the operation of the MRI apparatus and prevent the decrease of the S/N ratio.

According to this invention, there is provided an MRI apparatus comprising;
a gantry having an inner hollow portion;
a cradle on which an object lays and which is moved in vertical and horizontal directions so that the object is located in the inner hollow portion;
an RF coil for transmitting an RF pulse to the object on the cradle and receiving an MR signal from the object, the RF coil being connected to a connector provided in the cradle;
a transmitting-receiving unit for the RF coil, provided in the gantry;
an RF cable connected to the connector and the transmitting-receiving unit; and
a cable handling unit for handling the RF cable,
wherein the cable handling unit comprises a slack-preventing mechanism for winding the RF cable and feeding the RF cable according to a motion of the cradle.

Preferably the cable handling unit comprises a cable guide mechanism between the connector and the slack-preventing mechanism, for guiding the RF cable.

Furthermore preferably the cable guide mechanism comprises a stationary guide provided in the gantry and a moving guide, one end of which is linked to the stationary guide slidably and the other end of which is linked to the cradle rotatably.

Furthermore preferably the moving guide comprises a first link member linked to the cradle rotatably and a second link member, one end of which is linked to the first link member rotatably and the other of which is linked to the stationary guide slidably.

Preferably the slack-preventing mechanism comprises a reel for winding the RF cable and feeding the RF cable and a tension-imparting mechanism for imparting a tension to the RF cable.

Preferably the tension-imparting mechanism comprises a spring provided between the reel and the gantry, in which an elastic energy can be accumulated when the RF cable is fed from the reel and the accumulated elastic energy can drive the reel when the RF cable is winded in the reel.

The cable handling unit preferably comprises a twist-preventing mechanism for preventing a twist of the RF cable.

Preferably the twist-preventing mechanism comprises a reel, wherein the RF cable is winded loosely in the reel in a predetermined number of turns so that when the reel rotates, the number of turns decreases and when the reel rotates reversely, the number of turns increases.

BRIEF DESCRIPTION OF THE DRAWINGS

For a more complete understanding of this invention, reference will be made to the following detailed explanations in conjunction with the accompanying drawing in which.

DESCRIPTION OF THE PREFERRED EMBODIMENTS

Figure 1:
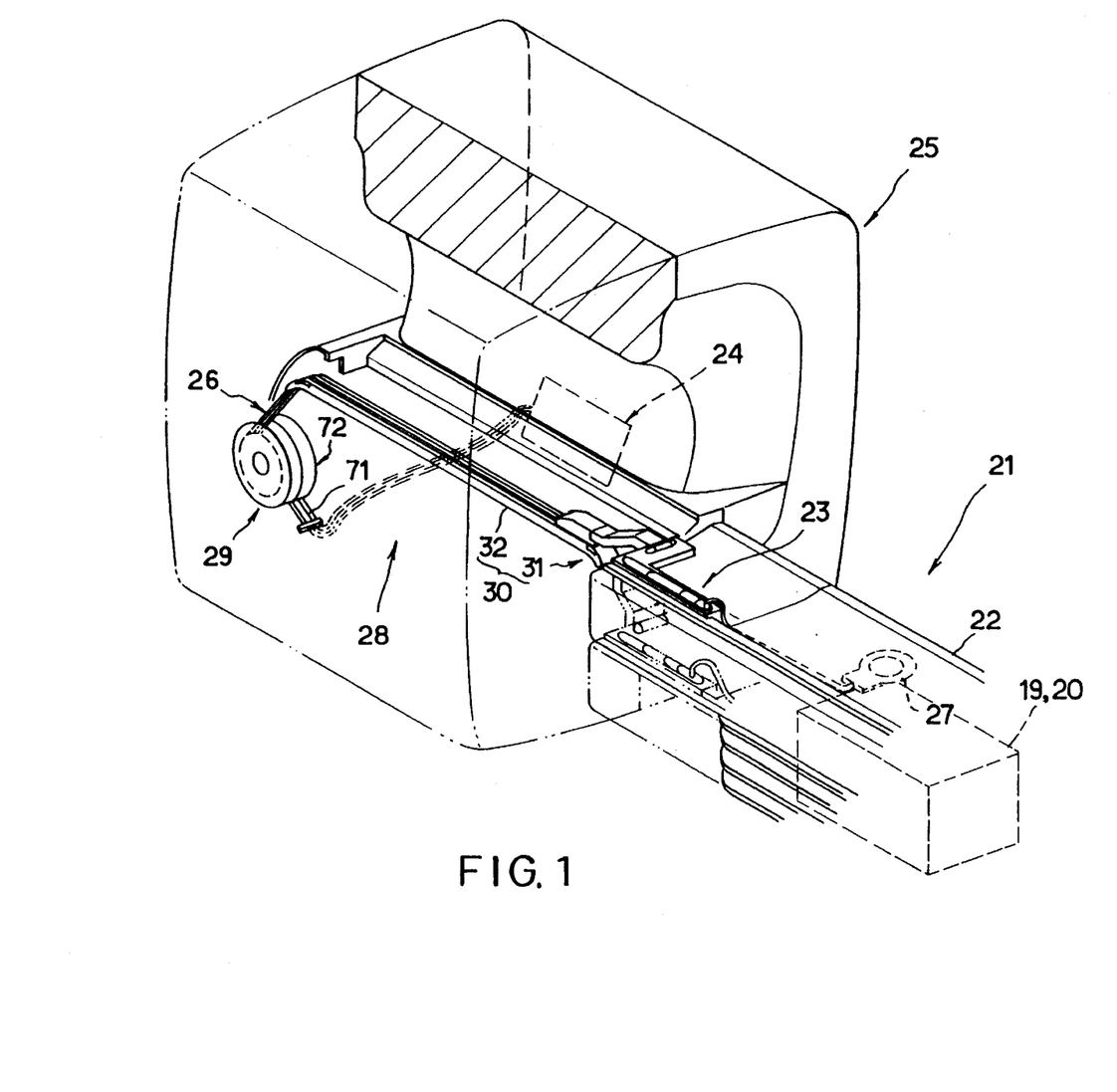
FIG. 1 is a perspective view showing an MR imaging apparatus embodying this invention, which is provided with a cable handling unit for handling said RF cable, comprising a slack-preventing mechanism, a cable guide mechanism and a twist-preventing mechanism.

Referring now to the accompanying drawing, the MR imaging apparatus, as shown in FIG. 1, comprises a patient couch 21 having a cradle 22 for laying a patient and a gantry 25 having a magnet, a gradient coil(not shown) and so on.

The cradle 22 is provided with a connector 23 for an RF coil 27 and the gantry 25 is provided with a transmitting-receiving unit 24 for the RF coil 27.

The connector 23 is electrically connected to one end of RF cable 26 and the other end of the RF cable 26 is connected to the transmitting-receiving unit 24.

The couch 21 comprises a lifting mechanism 19 for lifting the cradle 22 in a vertical direction so that the patient can easily lie on the cradle in a lower position(shown in a dotted line) and can be positioned in a predetermined level in an upper position(shown in a solid line).

Furthermore, the couch 21 comprises a moving mechanism 20 for moving the cradle 22 in a horizontal direction so that the patient can be moved into a cavity of the gantry 25 and drawn out from the cavity.

The connector 23 can be connected to various type of RF coils, for example, a head coil or a neck coil.

The RF coil 27 can transmit an RF pulse to the patient and receive an MR signal from the patient.

The transmitting-receiving unit 24 transmits an RF pulse to the RF coil 27 and amplify an MR signal received by the RF coil 27.

The MR imaging apparatus comprises a cable handling unit 28 for handling the RF cable 26.

The cable handling unit 28 comprises a slack-preventing mechanism 29 for winding the RF cable 26 and feeding the RF cable 26 according to a motion of the cradle 22 and a cable guide mechanism 30 between the connector 23 and the slack-preventing mechanism 29, for guiding the RF cable 26.

The cable guide mechanism 30 comprises a stationary guide 32 provided in the gantry 25 and a moving guide 31, one end of which is linked to the stationary guide 32 slidably and the other end of which is linked to the cradle 22 rotatably.

Figure 2:
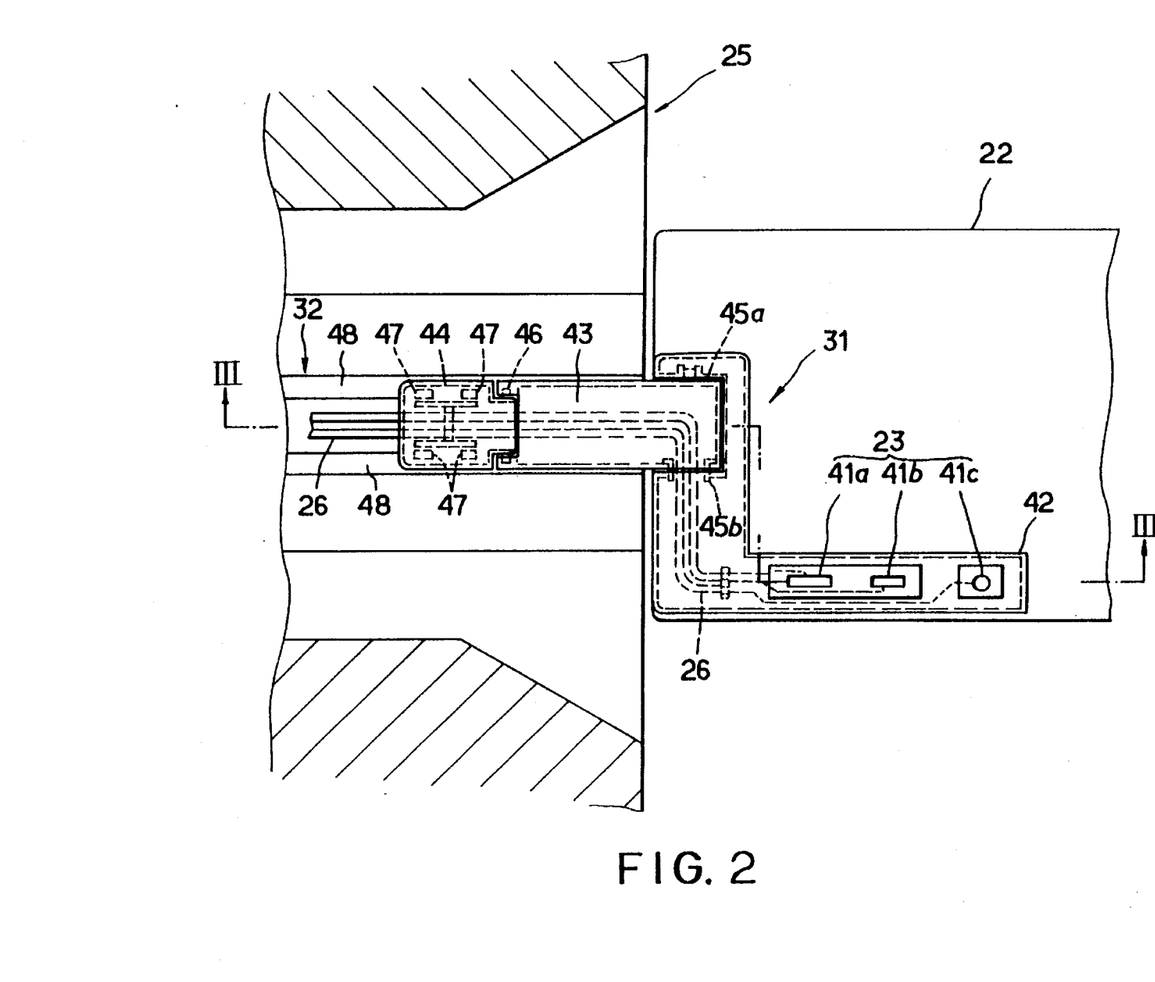
FIG. 2 is a plan view showing the cable guide mechanism.

FIG. 2 is a plan view showing the stationary guide 32 in the gantry 25 and the moving guide 31.

As shown in FIG. 2, the connector 23 is provided with a plurality of connector ports, for example, three connector ports 41a, 41b and 41c, which can be selected according to the types of the RF coil.

The connector 23 is mounted to the cradle 22 by means of a mount 42 and the RF cable 26 connected to the connector 23 are guided to the gantry 25 through an interior of the mount 42.

The moving guide 31 comprises a first link member 43 linked to the mount 42 of the cradle 22 rotatably and a second link member 44, one end of which is linked to the first link member 43 rotatably and the other end of which is linked to the stationary guide 32 slidably.

The first link member 43 is linked to the mount 42 by means of shafts 45a and 45b. The shaft 45b is a hollow body and the RF cable 26 can penetrate through the shaft 45b.

The other end of the first link member 43 is connected to the second member 44 by means of a shaft 46.

The second link member 44 comprises rollers 47 between which ribs 48 of the stationary guide 32 can be held slidably and the rollers 47 can run along the ribs 48.

The ribs 48 are shaped in a predetermined curvature so that the second link member 44 can run smooth according to a vertical motion of the cradle 22.

Figure 3:
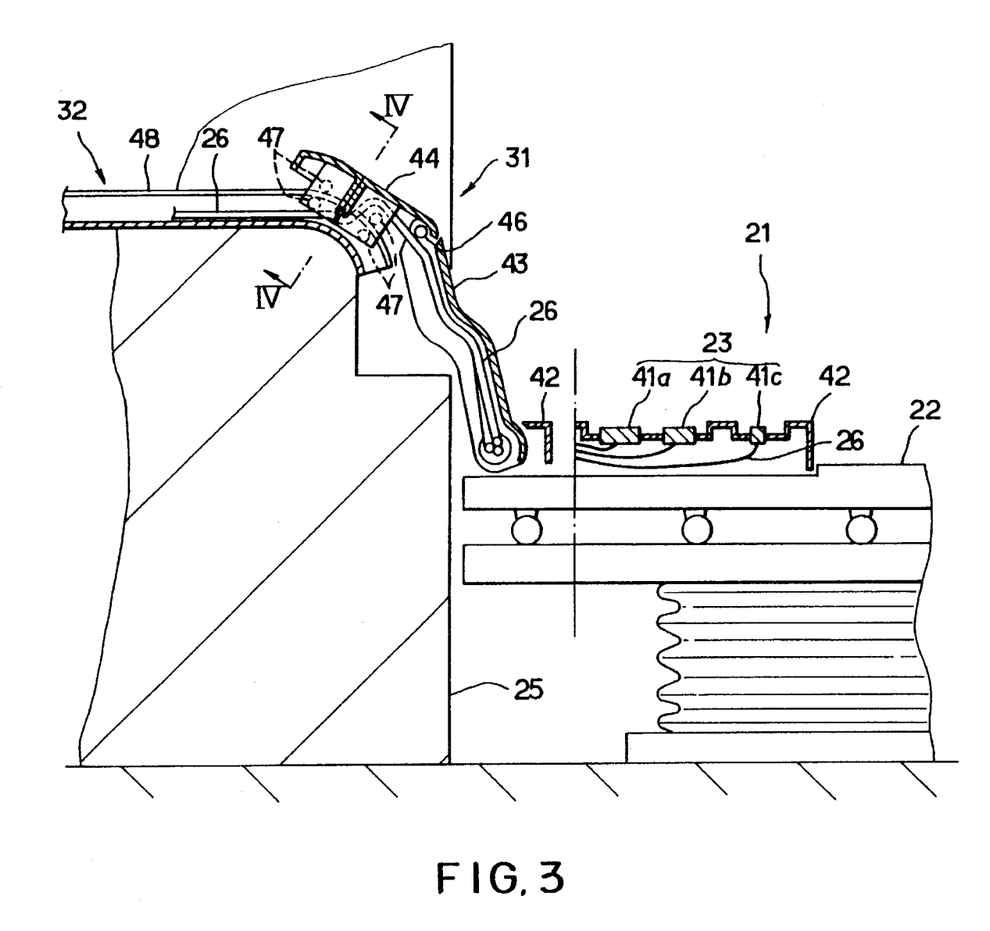
FIG. 3 is a cross sectional view taken along a line III—III of FIG. 2.

FIG. 3 is a cross sectional view taken along a line of FIG. 2.

As shown in FIG. 2 and FIG. 3, the RF cable 26 from the mount 42 are guided through an interior of the first link member 43 and the second link member 44 into an interior of the stationary guide 32.

Figure 4:
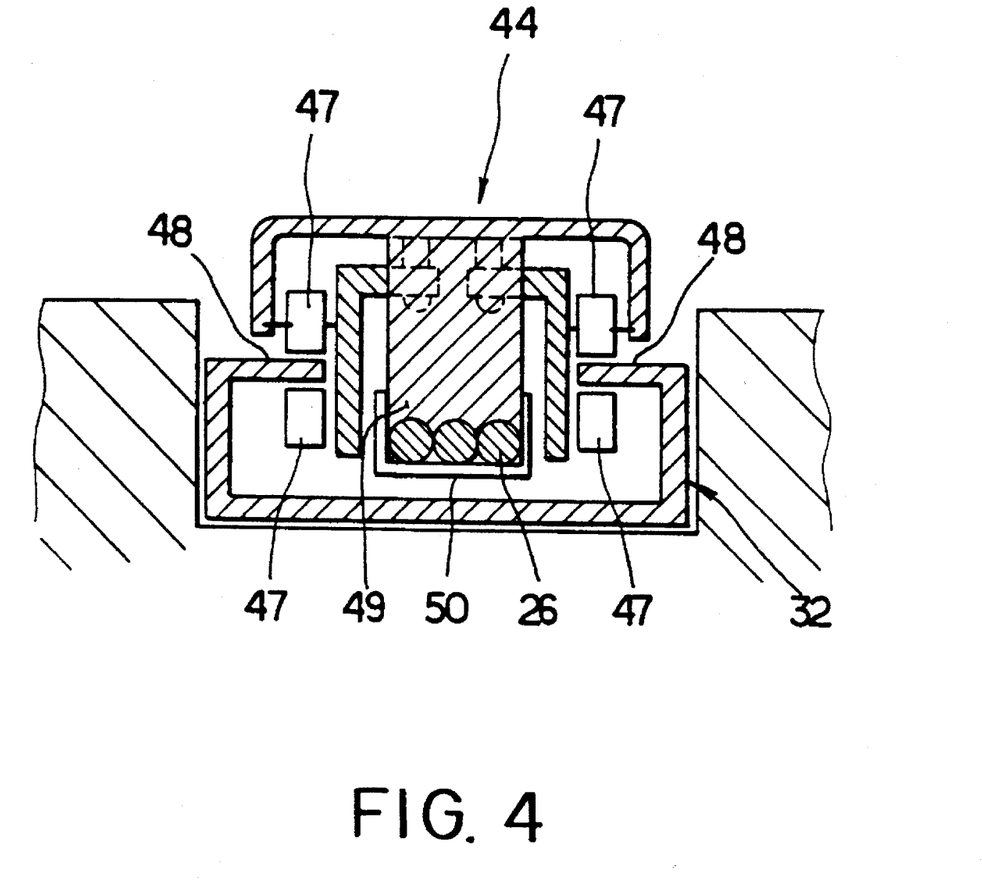
FIG. 4 is a cross sectional view taken along a line IV—IV of FIG. 3.

FIG. 4 is a cross sectional view taken along a line IV—IV of FIG. 3.

The rollers 47 provided in the second link member 44, holds the ribs 48 of the stationary guide 32 slidably.

The RF cables 26 are secured to a plate 49 by means of cable-securing member 50.

Figure 5:
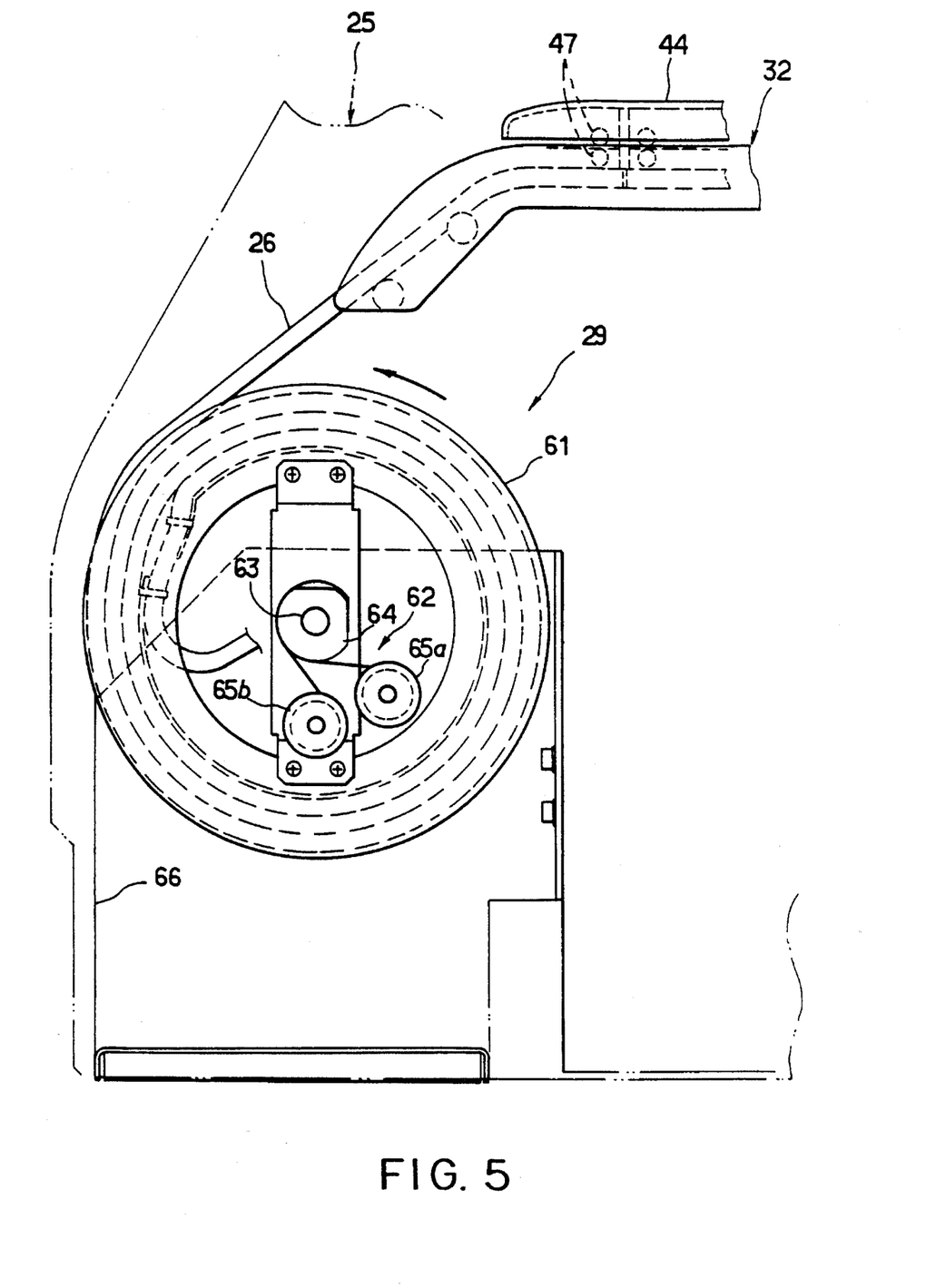
FIG. 5 is an elevational view showing the slack-preventing mechanism.

FIG. 5 is an elevational view showing the slack-preventing mechanism 29 for preventing the slack of the RF cable 26.

The slack-preventing mechanism 29 comprises a reel 61 for winding the RF cable 26 and feeding the RF cable 26 and a tension-imparting mechanism 62 for imparting a predetermined tensional load to the RF cable 26.

A shaft 63 of the reel 61 is mounted rotatably to a plate 66 fixed to the gantry 25.

The tension-imparting mechanism 62 comprises springs 65a and 65b, one-sided ends of which are secured to a portion of the shaft 63, the other-sided ends of which are secured to the gantry 25, which can accumulate an energy for rotating the reel 61 counterclockwise.

The springs 65a and 65b are preferably constant-tension springs for imparting a substantially constant tension to the reel 61 in any rotational position of the reel 61.

The cable handling unit 28 further comprises a twist-preventing mechanism 72 for preventing a twist of the RF cable 26, as shown in FIG. 1, provided between the transmitting-receiving unit 24 and the slacking-preventing mechanism 29.

Figure 6:
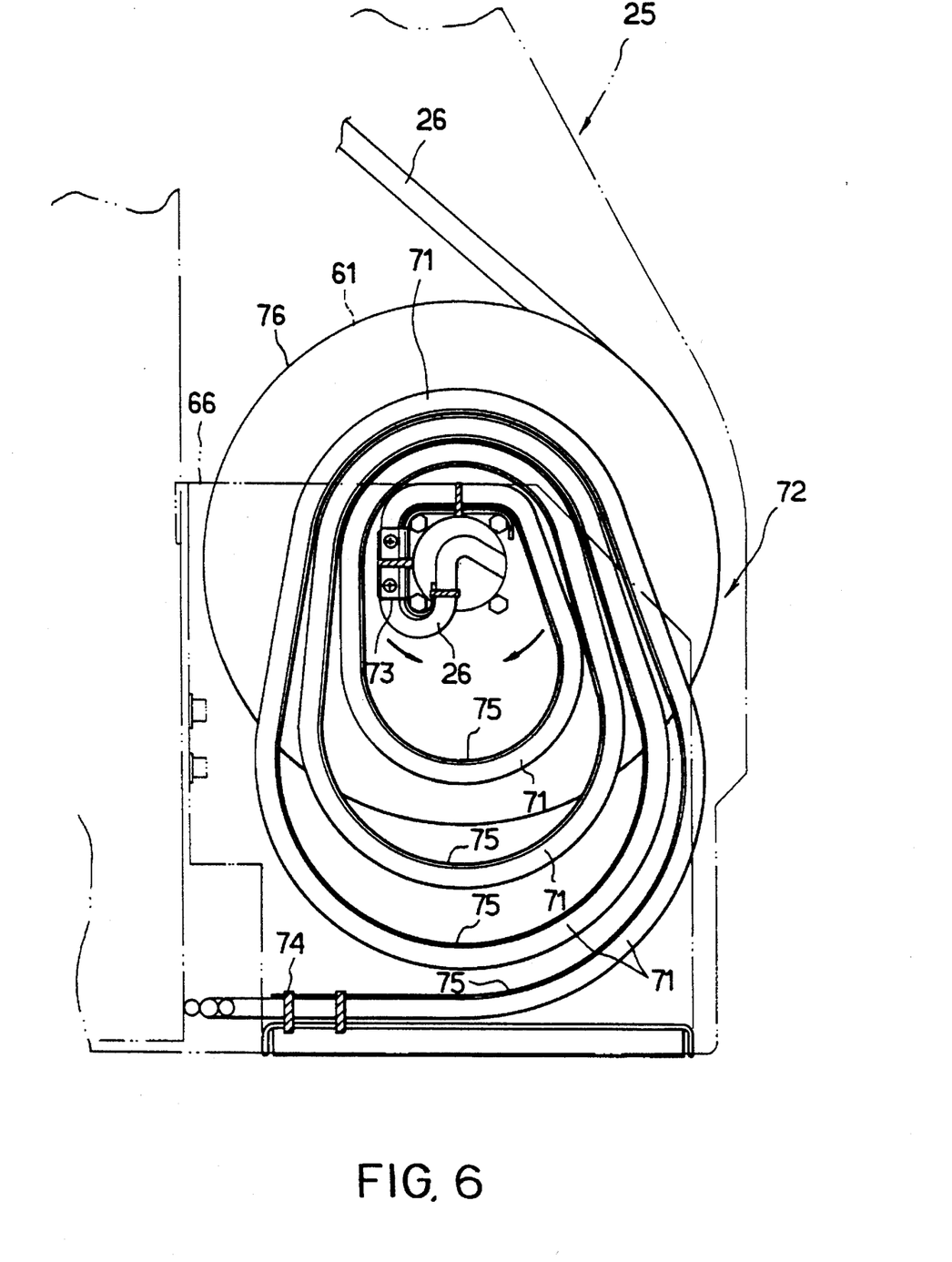
FIG. 6 is an elevational view showing the twist-preventing mechanism.

FIG. 6 is an elevational view showing the twist-preventing mechanism 72.

The twist-preventing mechanism 72 comprises a reel 76 located back of the reel 61, which is secured to the reel 61 coaxially so that the reel 76 can rotate together with the reel 61.

The reel 61 is not shown in FIG. 6 because the reel 61 cannot be seen behind the reel 76 but the RF cable 26 is not winded in the reel 76 but winded in the reel 61.

The RF cable 26 penetrates back of the reel 61, for example, through the hollow shaft 63 of the reel 61 and secured to the reel 76 in terms of a plate 73. Furthermore, the RF cable 26 is winded in the reel 76 and fixed to the gantry 25 by a plate 74 and connected to the transmitting-receiving unit 24 (not shown in FIG. 6).

The RF cable 71 between the plate 73 and the plate 74 is winded loosely in the reel 76 in a predetermined number of turns so that when the reel 76 rotates clockwise, the number of turns decreases and when the reel 76 rotates counterclockwise, the number of turns increases.

Therefore, the twist of the RF cable 71 by the rotation of the reel 61 and 76 can be prevented.

A predetermined sheet 75 which surface is smooth, is located between the adjacent turns of the RF cable 71 so that a friction between the adjacent turns can be decreased.

Therefore, the RF cable 71 can be winded or feeded smoothly and the reel 76 can rotate smoothly.

The sheet 75 may be preferably made of Teflon.

In the operation of the MR imaging apparatus, first of all, if the patient can lie on the couch 21, the patient lies on the cradle 22 of the couch 21 in the lower position shown in FIG. 3.

The cradle 22, then, is lifted to the upper position shown in FIG. 1 using the lifting mechanism 19.

As shown in FIG. 3, while lifting the cradle 22, a right end of the first link member 43 linked to the mount 42 of the cradle 22 rotatably is moved up and the second link member 44 linked to the first link member 43 rotatably is slided left along the rib 48 of the stationary guide 32.

The RF cable 26 connected to the connector port 41a, 41b and 41c, run through the mount 42 and the first link member 43 and fixed to the plate 49 of the second link member 44 and therefore the second link member 44 moves the RF cable 26 left into the stationary guide 32.

After the cradle 22 has been lifted to the upper position shown in FIG. 1, the cradle 22 is moved left and fed into the cavity of the gantry 25 using the moving mechanism 20 provided in the couch 21 to locate the patient to a predetermined position for imaging.

As the horizontal moving of the cradle 22, as shown in FIG. 1, the moving guide 31 mounted to the cradle 22, is moved along the stationary guide 32 mounted to the gantry 25 and the RF cable 26 is fed to the slacking-preventing mechanism 29.

The tension-imparting mechanism 62 provided in the slacking-preventing mechanism 29, as shown in FIG. 5, drives the reel 61 in counterclockwise and the reel 61 winds the RF cable 26 with no slacking according to the horizontal travel of the second link member 44.

As the reel 61 rotates, as shown in FIG. 6, the reel 76 provided in the twist-preventing mechanism 72 rotates in clockwise interlockingly to the motion of the reel 61.

The reel 76 rotates smooth because the sheets 75 are located between the adjacent turns of the RF cable 71 and decreases the number of turns in the RF cable 71 with no twisting of the RF cable 71.

Therefore, the RF cable 71 can be prevented from a damage caused by a twisting in the long term.

After acquiring of imaging data, the cradle 22 is moved right in FIG. 1 and drawn from the cavity of the gantry 25.

As the cradle 22 is moved right, the reel 61 feeds the RF cable 26 and the second link member 44 provided in the moving guide 31, travels along the rib 48 provided in the stationary guide 32.

The tension-imparting mechanism 62 provided in the slacking-preventing mechanism 29, accumulates an elastic energy.

As the reel 61 rotates, the reel 76 provided in the twist-preventing mechanism 72 rotates in counterclockwise in FIG. 6 interlockingly to the motion of the reel 61 and increases the number of turns in the RF cable 71 with no twisting of the RF cable 71.

After the cradle 22 is moved to a predetermined horizontal position, the cradle 22 is lowered from the position to a predetermined lower position.

As above described, according to this invention, the RF cable can be located at a distance from the RF coil and an interaction between the RF coil and the RF cable can be decreased.

Thus, the MR image can be acquired in a high S/N ratio.

Furthermore, according to this invention, the cable handling unit comprises a slack-preventing mechanism for winding the RF cable and feeding the RF cable according to the motion of the cradle.

Therefore, the RF cable can be guided with no slacking when the cradle is moved along a vertical or horizontal direction.

Furthermore, according to this invention, the RF cable handling unit comprises a cable guide mechanism between the connector and the slack-preventing mechanism, for guiding the RF cable.

Therefore, the RF cable can be handled in a predetermined route and the cradle can be moved in a vertical direction with no detaching of the RF cable from the connector.

Thus, the MR imaging apparatus can be operated more easily and the through put for acquiring MR imaging data, can be increased.

Furthermore, according to this invention, the slack-preventing mechanism comprises a reel for winding the RF cable and feeding the RF cable.

Therefore, a space required for an installation of the cable handling apparatus can be minimized.

Furthermore, according to this invention, the slack-preventing mechanism comprises a tension-imparting mechanism for imparting a predetermined tensional load to the reel.

Therefore, slacking of the RF cable can be prevented.

Still furthermore, according to this invention, the cable handling unit comprises a twist-preventing mechanism and therefore the RF cable can be prevented from twisting.

In the above embodiment, the number of RF cable is not referred to but the number may be increased by adjusting the dimension of the moving guide, the stationary guide and so on.

In the above embodiment, the tension-imparting mechanism is provided with a spring which can generate a substantially constant tensional load but any other type of spring may be used.

In the above embodiment, the sheets are located between the adjacent turns of the RF cable but may by omitted if the surface of the RF cable is treated in a predetermined finishing so that the friction can be decreased.

In the above embodiment, the slacking-preventing mechanism and the twist-preventing mechanism are provided in the gantry but these mechanism may be provided in the couch if the interaction between the RF coil and the RF cable can be ignored.

For example, the stationary guide may be provided in a predetermined portion of the couch and the moving guide linked to the stationary guide, may be provided in a back of the cradle faced to the portion.

What is claimed is:

1. A magnetic resonance (MR) imaging apparatus comprising:

a gantry having an inner hollow portion;

a cradle on which an object lays;

means for driving the cradle in vertical and horizontal directions to move the object into the inner hollow portion of the gantry;

an RF coil for at least receiving an MR signal from the object on the cradle, said RF coil being connected to a connector provided in the cradle;

a receiving unit for said RF coil;

an RF cable connected to the connector and the receiving unit; and a cable handling unit comprising a slack preventing mechanism means for winding the RF cable including a reel means around which the RF cable is wound, a tension imparting means for imparting a tension in a direction along which the RF cable is wound around the reel means, and a cable guide mechanism means disposed between the connector and the slack preventing mechanism means for guiding the RF cable, said cable guide mechanism means comprising a stationary guide provided in the gantry and a moving guide, one end of which is slidably linked to the stationary guide and the other end of which is rotatably linked to the cradle, wherein the RF cable is wound around the reel means or fed therefrom by an amount corresponding to an amount of displacement of the cradle with respect to the gantry.

2. An MR imaging apparatus according to claim 1, wherein said moving guide comprises a first link member linked to said cradle rotatably and a second link member having one end linked to said first link member rotatably and the other end linked to said stationary guide slidably.

3. An MR imaging apparatus according to claim 1, wherein said tension-imparting means comprises a spring provided between said reel means and said gantry, in which an elastic energy can be accumulated when said RF cable is fed from said reel means and said accumulated elastic energy can drive said reel means when said RF cable is wound in said reel means.

4. An MR imaging apparatus according to claim 1, wherein said cable handling unit comprises a twist-preventing mechanism means for preventing a twist of said RF cable.

5. An MR imaging apparatus according to claim 4, wherein said twist-preventing mechanism means comprises a reel rotated according to a motion of said cradle, wherein said reel winds said RF cable loosely in a predetermined number of turns so that when said reel rotates in a predetermined direction, the number of turns decreases and when said reel rotates reversely, the number of turns increases.

* * * * *